US012727789B2

(12) United States Patent
Nakamura

(10) Patent No.: US 12,727,789 B2
(45) Date of Patent: Sep. 8, 2026

(54) OPTICAL COHERENCE TOMOGRAPHY ANALYSIS APPARATUS, OPTICAL COHERENCE TOMOGRAPHY ANALYSIS METHOD, AND NON-TRANSITORY RECORDING MEDIUM

(71) Applicant: NEC Corporation, Tokyo (JP)

(72) Inventor: Shigeru Nakamura, Tokyo (JP)

(73) Assignee: NEC CORPORATION, Tokyo (JP)

( * ) Notice: Subject to any disclaimer, the term of this patent is extended or adjusted under 35 U.S.C. 154(b) by 245 days.

(21) Appl. No.: 18/722,677

(22) PCT Filed: Dec. 24, 2021

(86) PCT No.: PCT/JP2021/048237
§ 371 (c)(1),
(2) Date: Jun. 21, 2024

(87) PCT Pub. No.: WO2023/119631
PCT Pub. Date: Jun. 29, 2023

(65) Prior Publication Data
US 2025/0064346 A1 Feb. 27, 2025

(51) Int. Cl.
*A61B 5/1172* (2016.01)
*A61B 5/00* (2006.01)
*G06T 7/30* (2017.01)

(52) U.S. Cl.
CPC .......... *A61B 5/1172* (2013.01); *A61B 5/0066* (2013.01); *G06T 7/30* (2017.01);
(Continued)

(58) Field of Classification Search
None
See application file for complete search history.

(56) References Cited

U.S. PATENT DOCUMENTS 8,224,064 B1 * 7/2012 Hassebrook ......... G06V 10/145 356/3
2009/0208070 A1 8/2009 Fourre et al.
(Continued)

FOREIGN PATENT DOCUMENTS

JP 2019-519034 A 7/2019
WO 2009/112717 A1 9/2009
(Continued)

OTHER PUBLICATIONS

Costa, Henrique SG, et al. "Towards biometric identification using 3D epidermal and dermal fingerprints." 2016 IEEE International Conference on Image Processing (ICIP). IEEE, 2016 (Year: 2016).*
(Continued)

*Primary Examiner* — Henok Shiferaw
*Assistant Examiner* — Xiaomao Ding
(74) *Attorney, Agent, or Firm* — Sughrue Mion, PLLC

(57) ABSTRACT

An optical coherence tomography analysis apparatus includes: an acquisition unit that performs optical coherence tomography by applying a light beam, and that acquires three-dimensional luminance data about the skin; a position extraction unit that extracts an epidermis position, for each tomography image obtained by scanning in a fast axis
(Continued)

direction of the light beam, in the three-dimensional luminance data about the skin; a connection unit that generates connected three-dimensional data, by adjusting relative positions between tomography images and connecting the tomography images, on the basis of an extraction result of the epidermis position; a flattening unit that generates flattened three-dimensional data, by performing transformation processing of flattening epidermis on the connected three-dimensional data, on the basis of an extraction result of the epidermis position; and a pattern extraction unit that extracts a pattern of the skin corresponding to a predetermined extraction depth, from the flattened three-dimensional data.

7 Claims, 14 Drawing Sheets

(52) U.S. Cl.
CPC ............... *G06T 2207/10101* (2013.01); *G06T 2207/30088* (2013.01)

(56) References Cited

U.S. PATENT DOCUMENTS

2017/0083742 A1* 3/2017 Lamare .................. G06V 40/13
2018/0173936 A1 6/2018 Mizoguchi
2019/0121791 A1 4/2019 Lee
2021/0004971 A1* 1/2021 Fukuma ............... A61B 3/0025
2022/0139105 A1 5/2022 Ono et al.
2022/0277498 A1 9/2022 Ono et al.
2023/0102868 A1 3/2023 Nakamura

FOREIGN PATENT DOCUMENTS

WO 2016/204176 A1 12/2016
WO 2020/170439 A1 8/2020
WO 2021/019788 A1 2/2021
WO 2021/192117 A1 9/2021

OTHER PUBLICATIONS

International Search Report for PCT Application No. PCT/JP2021/048237, mailed on Mar. 22, 2022.

* cited by examiner (a)

(b)

OPTICAL COHERENCE TOMOGRAPHY ANALYSIS APPARATUS, OPTICAL COHERENCE TOMOGRAPHY ANALYSIS METHOD, AND NON-TRANSITORY RECORDING MEDIUM

This application is a National Stage Entry of PCT/JP2021/048237 filed on Dec. 24, 2021, the contents of all of which are incorporated herein by reference, in their entirety.

TECHNICAL FIELD

This disclosure relates to technical fields of an optical coherence tomography analysis apparatus, an optical coherence tomography analysis method, and a recording medium.

BACKGROUND ART

A known apparatus of this type images a pattern of a skin/a pattern of dermatoglyphics of a living body (e.g., a fingerprint or the like, etc.). For example, Patent Literature 1 discloses a fingerprint imaging apparatus that acquires a fingerprint image of epidermis in a noncontact manner, while allowing a fingertip to pass through a predetermined space without touching a glass plate or the like. Furthermore, Patent Literatures 2 to 4 disclose a fingerprint imaging apparatus that performs a three-dimensional tomography imaging of a fingertip and acquires a fingerprint image of dermis, by using an optical coherence tomography (OCT) technique/technology.

CITATION LIST

Patent Literature

Patent Literature 1: International Publication No. WO2009/112717A1

Patent Literature 2: International Publication No. WO2016/204176A1

Patent Literature 3: International Publication No. WO2020/170439A1

Patent Literature 4: International Publication No. WO2021/019788A1

SUMMARY

Technical Problem

This disclosure aims to improve the techniques/technologies disclosed in Citation List.

Solution to Problem

An optical coherence tomography analysis apparatus according to an example aspect of this disclosure includes: an acquisition unit that performs optical coherence tomography by applying a light beam to a skin while performing two-dimensional scanning, and that acquires three-dimensional luminance data about the skin; a position extraction unit that extracts an epidermis position of the skin, for each tomography image obtained by scanning in a fast axis direction of the light beam, in the three-dimensional luminance data about the skin; a connection unit that generates connected three-dimensional data, by adjusting relative positions between tomography images and connecting the tomography images, on the basis of an extraction result of the epidermis position of the skin; a flattening unit that generates flattened three-dimensional data, by performing transformation processing of flattening epidermis on the connected three-dimensional data, on the basis of an extraction result of the epidermis position of the skin; and a pattern extraction unit that extracts a pattern of the skin corresponding to a predetermined extraction depth, from the flattened three-dimensional data.

An optical coherence tomography analysis method according to an example aspect of this disclosure includes: performing optical coherence tomography by applying a light beam to a skin while performing two-dimensional scanning, and acquiring three-dimensional luminance data about the skin; extracting an epidermis position of the skin, for each tomography image obtained by scanning in a fast axis direction of the light beam, in the three-dimensional luminance data about the skin; generating connected three-dimensional data, by adjusting relative positions between tomography images and connecting the tomography images, on the basis of an extraction result of the epidermis position of the skin; generating flattened three-dimensional data, by performing transformation processing of flattening epidermis on the connected three-dimensional data, on the basis of an extraction result of the epidermis position of the skin; and extracting a pattern of the skin corresponding to a predetermined extraction depth, from the flattened three-dimensional data.

A recording medium according to an example aspect of this disclosure is a recording medium on which a computer program that allows at least one computer to execute an optical coherence tomography analysis method is recorded, the optical coherence tomography analysis method including: performing optical coherence tomography by applying a light beam to a skin while performing two-dimensional scanning, and acquiring three-dimensional luminance data about the skin; extracting an epidermis position of the skin, for each tomography image obtained by scanning in a fast axis direction of the light beam, in the three-dimensional luminance data about the skin; generating connected three-dimensional data, by adjusting relative positions between tomography images and connecting the tomography images, on the basis of an extraction result of the epidermis position of the skin; generating flattened three-dimensional data, by performing transformation processing of flattening epidermis on the connected three-dimensional data, on the basis of an extraction result of the epidermis position of the skin; and extracting a pattern of the skin corresponding to a predetermined extraction depth, from the flattened three-dimensional data.

DESCRIPTION OF EXAMPLE EMBODIMENTS

Hereinafter, an optical coherence tomography analysis apparatus, an optical coherence tomography analysis method, and a recording medium according to example embodiments will be described with reference to the drawings.

First Example Embodiment

An optical coherence tomography analysis apparatus according to a first example embodiment will be described with reference to FIG. 1 to FIG. 9.

(Hardware Configuration)

Figure 1:
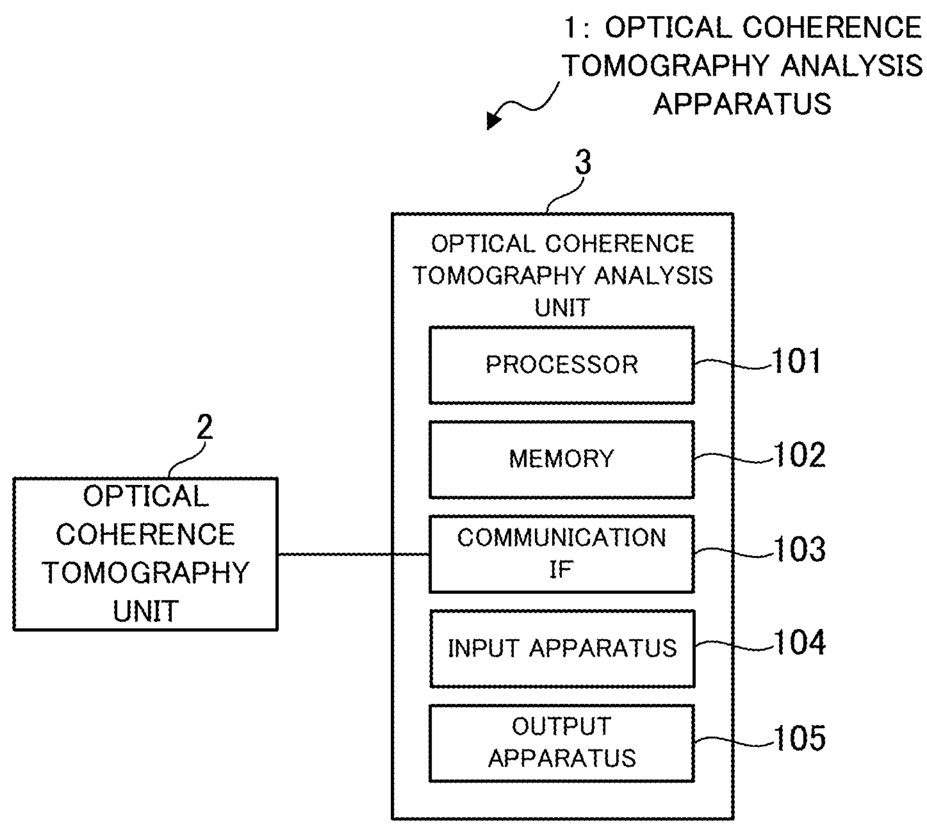
FIG. 1 is a block diagram illustrating a hardware configuration of an optical coherence tomography analysis apparatus according to a first example embodiment.

First, with reference to FIG. 1, a hardware configuration of the optical coherence tomography analysis apparatus according to the first example embodiment will be described. FIG. 1 is a block diagram illustrating an example of the hardware configuration of the optical coherence tomography analysis apparatus according to the first example embodiment.

In FIG. 1, an optical coherence tomography analysis apparatus 1 according to the first example embodiment is configured as an apparatus capable of imaging a skin of a living body by using a three-dimensional measurement technique/technology such as OCT, and extracting a pattern of the skin/a pattern of dermatoglyphics from three-dimensional data obtained by the imaging. The type of the pattern of the skin is not particularly limited, and may be, for example, a fingerprint, a palm print, or the like. Hereinafter, for convenience of description, extraction of a fingerprint will be described. The optical coherence tomography analysis apparatus 1 according to the first example embodiment includes an optical coherence tomography unit 2 and an optical coherence tomography analysis unit 3. Units of the optical coherence tomography analysis apparatus 1 may be connected to each other through a not-illustrated bus, wires, drive apparatuses or the like.

The optical coherence tomography unit 2 is configured to image the skin of a living body, by using the three-dimensional measurement technique/technology such as OCT. The optical coherence tomography unit 2 is configured to be output three-dimensional luminance data obtained by the imaging, to the optical coherence tomography analysis unit 3. A specific configuration of the optical coherence tomography unit 2 will be described in detail later.

The optical coherence tomography analysis unit 3 is configured to extract the pattern of the skin of a living body (e.g., a fingerprint of epidermis or dermis, etc.), by analyzing the three-dimensional luminance data acquired from the optical coherence tomography unit 2. The optical coherence tomography analysis unit 3 may be, for example, a computer such as a data processing server, a desktop PC (Personal Computer), a notebook PC, and a tablet PC. The optical coherence tomography analysis unit 3 includes a processor 101, a memory 102, a communication IF (Interface) 103, an input apparatus 104 and an output apparatus 105, as a computer for arithmetic operation/calculation, control, and storage.

The processor 101 is a processing apparatus including one or more arithmetic processing circuits, such as, for example, a CPU (Central Processing Unit), a GPU (Graphics Processing Unit), a FPGA (Field-Programmable Gate Array), and an ASIC (Application Specific Integrated Circuit). The processor 101 performs a predetermined arithmetic operation in accordance with a program stored in the memory 102 or the like, and also has a function of controlling each part/unit of the optical coherence tomography analysis unit 3.

The memory 102 may include a volatile storage medium that provides a temporary/transitory memory area required for operation of the processor 101, and a nonvolatile storage medium that stores processing target data and information such as an operation program of the optical coherence tomography analysis unit 3, in a non-transitory manner. An example of the volatile storage medium includes a RAM (Random Access Memory). An example of the nonvolatile storage medium includes a ROM (Read Only Memory), a HDD (Hard Disk Drive), a SSD (Solid State Drive), a flash memory, and the like.

The communication I/F 103 is a communication interface based on standards such as Ethernet (registered trademark), Wi-Fi (registered trademark), and Bluetooth (registered trademark). The communication IF 103 is a module for communicating with another device such as the optical coherence tomography unit 2.

The input apparatus 104 is a keyboard, a pointing device, a key, a button, or the like, and is used by a user to operate the optical coherence tomography analysis unit 3. An example of the pointing device includes a mouse, a trackball, a touch panel, a pen tablet, and the like.

The output apparatus 105 is, for example, an apparatus that presents information to a user, such as a display apparatus and a speaker. An example of the display apparatus includes a liquid crystal display, an OLED (Organic Light Emitting Diode) display, and the like. The input apparatus 104 and the output apparatus 105 may be integrally formed as a touch panel.

The hardware configuration illustrated in FIG. 1 is an example, and another apparatus may be added, and a part of the apparatuses may not be provided. In addition, a part of the apparatuses may be replaced by another apparatus having a similar/same function. In addition, a part of the functions in the present example embodiment may be provided by another apparatus through a network. The functions in the present example embodiment may be realized by being distributed into a plurality of apparatuses. For example, the optical coherence tomography unit 2 and the optical coherence tomography analysis unit 3 may be an integral apparatus. Thus, the hardware configuration illustrated in FIG. 1 may be changeable as appropriate.

(Configuration of Optical Coherence Tomography Unit)

Figure 2:
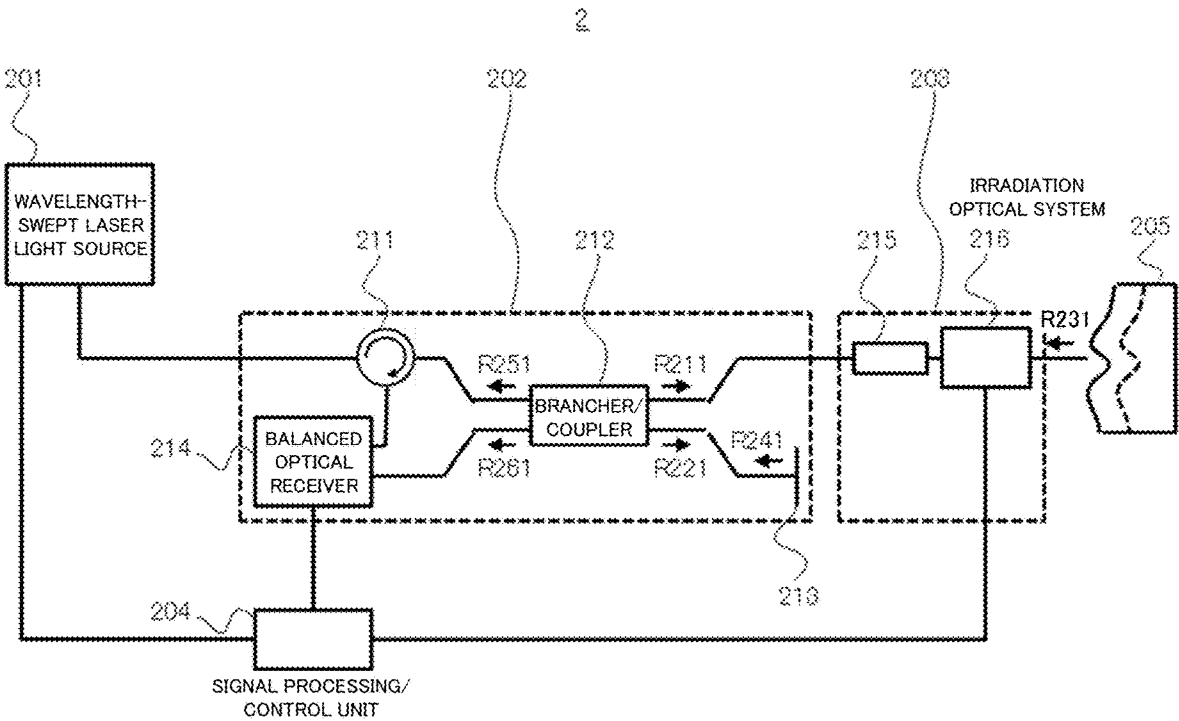
FIG. 2 is a schematic diagram illustrating a configuration example of an optical coherence tomography unit according to the first example embodiment.

Next, with reference to FIG. 2, a configuration of the optical coherence tomography unit 2 according to the first example embodiment will be specifically described. FIG. 2 is a schematic diagram illustrating a configuration example of the optical coherence tomography unit according to the first example embodiment. The configuration diagram illustrated in FIG. 2 illustrates only an example of a measuring instrument using the OCT technique/technology, and a measuring instrument configuration other than this may be also possible.

The OCT technique/technology includes: identifying a position of apart (a light scattering point) where object light is scattered in a measurement target in an optical axis direction, i.e., a depth direction, by using an interference between the object light and reference light; and acquiring structural data spatially resolved in the depth direction of an inside of the measurement targe. The OCT technique/technology includes Time Domain (TD-OCT) and Fourier Domain (FD-OCT), but the FD-OCT is more promising in terms of high speed and high sensitivity. In the FD-OCT, an interference light spectrum in a wide wavelength band is measured in the interference of the object light and the reference light, and is Fourier-transformed to acquire the structural data in the depth direction. A method of acquiring the interference light spectrum includes Spectral Domain (SD-OCT) using a spectrometer, and Swept Source (SS-OCT) using a light source for sweeping a wavelength.

Furthermore, by scanning an irradiation position of an object light beam in an in-plane direction perpendicular to the depth direction of the measurement target, it is possible to acquire tomography structural data spatially resolved in the in-plane direction and spatially resolved in the depth direction, i.e., three-dimensional tomography structural data on the measurement target.

FIG. 2 illustrates the optical coherence tomography unit 2 in the SS-OCT. In the optical coherence tomography unit 2, a wavelength-swept light pulse is generated by a wavelength-swept laser light source 201. Light emitted from the wavelength-swept laser light source 201 is applied and scattered on a measurement target 205 through a light interference/light receiving unit 202 and a light beam scanning unit 203. A part of the scattered light returns to the light interference/light receiving unit 202, and is subjected to photoelectric conversion. An electric signal outputted from the light interference/light receiving unit 202 is digitized by a signal processing/control unit 204, and is transmitted to the optical coherence tomography analysis unit 3.

The wavelength-swept laser light source 201 generates a light pulse whose wavelength is increased from 1250 nm to 1350 nm during a duration of 5 μs, and generates this light pulse every 10 μs at a repetition frequency of 100 kHz.

In the light interference/light receiving unit 202, the light emitted from the wavelength-swept laser light source 201 is inputted to a brancher/coupler 212 through a circulator 211. In the brancher/coupler 212, the inputted light is branched into object light R211 and reference light R221. The object light R211 is applied to the measurement target 205 through a fiber collimator 215 and an irradiation optical system 216 including a scanning mirror and a lens. Object light R231 scattered by the measurement target 205 returns to the brancher/coupler 212. On the other hand, reference light R221 returns to the brancher/coupler 212 through a reference light mirror 213. Therefore, in the brancher/coupler 212, the object light R231 scattered from the measurement target 205 interferes with reference light R241 reflected from the reference light mirror 213, thereby to generate rays of interfere light R251 and R261. That is, an intensity ratio of the interference light R251 and the interference light R261 is determined by a phase difference between the object light R231 and the reference light R241. The interference light R251 is inputted to a two-input balanced optical receiver 214 through the circulator 211, and the interferometric light R261 is inputted directly to the two-input balanced optical receiver 214. A voltage corresponding to an intensity difference between the interference light R251 and the interference light R261 is outputted from the balanced optical receiver 214, and is inputted to the signal processing/control unit 204.

The signal processing/control unit 204 generates interference light spectrum data, on the basis of information about a change in wavelength of the emitted light from the wavelength-swept laser light source 201 and information about a change in the intensity ratio of the interference light R251 and the interference light R261. The interference light spectrum data are Fourier-transformed, thereby acquire data indicating the intensity of backscattered light (object light) at different positions in the depth direction (also referred to as a "Z direction"). Hereinafter, an operation of acquiring the data indicating the intensity of the backscattered light (object light) in the depth direction (Z direction) at a certain position of the measurement target, is referred to as "A-scan". Since an A-scan waveform is generated every 10 μs at a repetition frequency of the light pulse, an electric signal with a repetition frequency of 100 kHz is supplied as an A-scan trigger signal from the wavelength-swept laser light source 201 to the signal processing/control unit 204. As an A-scan waveform, a waveform indicating object light backscatter intensity at Nz points, is obtained.

In addition, an illumination position of the object light beam R231 is scanned on the measurement target 205 by the irradiation optical system 216. The signal processing/control unit 204 controls the irradiation optical system 216 in response to the A-scan trigger signal supplied from the wavelength-swept laser light source 201, and moves the irradiation position of the object light beam R231 in a scanning line direction (a fast axis direction of the scanning, an X direction). By repeating the A-scan operation and connecting the A-scan waveforms at the respective irradiation positions of the object light, a map of the intensity of two-dimensional backscattered light (object light) in the scanning line direction and in the depth direction, is obtained as a tomography image. Hereinafter, an operation of repeating the A-scan operation in the scanning line direction (the fast axis direction of the scanning, the X direction) and connecting measurement results, is referred to as "B-scan". In a case where there are Nx irradiation positions of the object light beam for each B-scan, the tomography image by the B-scan is two-dimensional luminance data indicating the object light backscatter intensity at Nz×Nx points.

Furthermore, by repeating the B-scan operation while the irradiation optical system 216 moves the irradiation position of the object light beam R231 not only in the scanning line direction, but also in a direction perpendicular to the scanning line (a slow axis direction of the scanning, a Y direction) and by and connecting B-scan measurement results, three-dimensional tomography structural data are obtained. Hereinafter, an operation of repeating the B-scan operation in the direction perpendicular to the scanning line (Y direction) and connecting the measurement results, is referred to as "C-scan". When the number of times of the B-scan per C-scan is Ny, the tomography structural data obtained by the C-scan are three-dimensional luminance data indicating the object light backscatter intensity at Nz×Nx×Ny points.

In a case where there are 300 irradiation positions of the object light beam in the X direction and 300 irradiation positions of the object light beam in the Y direction, for example, a time required for one B scan is 3 ms because it is 300 times of the A scan, and a time required for one C scan is 900 ms because it is 300 times of the B scan. In a case of measuring a finger of a person in a noncontact manner, it seems to be possible to reduce the amount of movement of the finger during 3 ms, but it is hard to reduce the amount of movement of the finger during 900 ms.

(Functional Configuration of Optical Coherence Tomography Analysis Unit)

Figure 3:
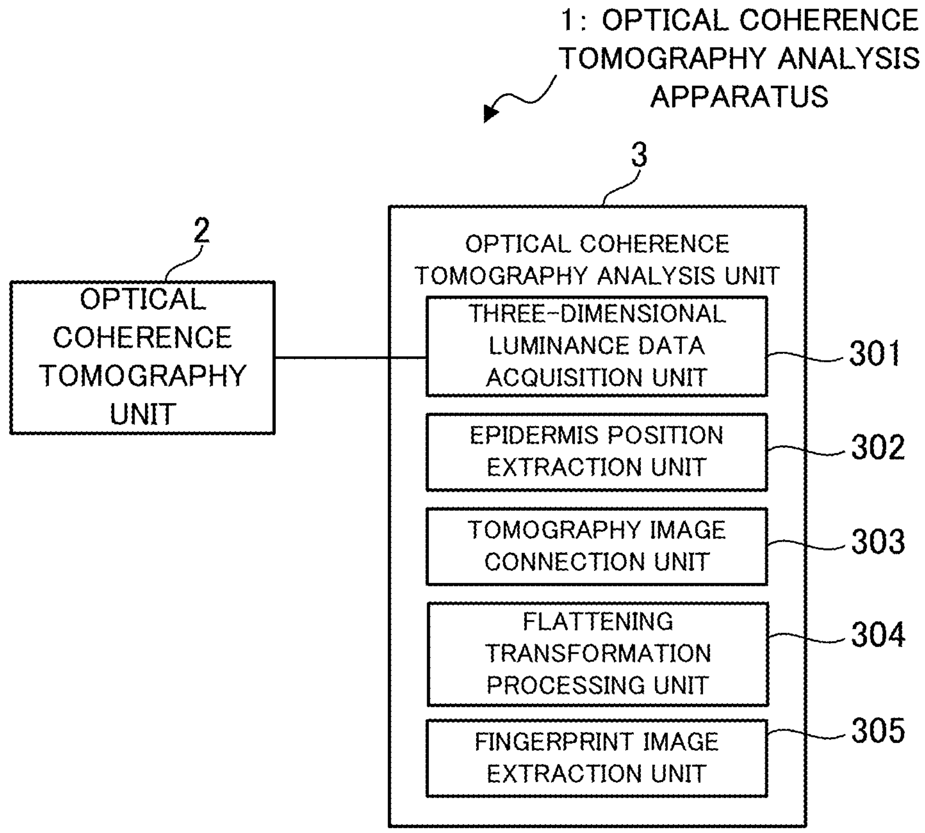
FIG. 3 is a block diagram illustrating a functional configuration of an optical coherence tomography analysis unit according to the first example embodiment.

Next, with reference to FIG. 3, a functional configuration of the optical coherence tomography analysis unit 3 according to the first example embodiment will be described. FIG. 3 is a block diagram illustrating the functional configuration of the optical coherence tomography analysis unit according to the first example embodiment.

As illustrated in FIG. 3, the optical coherence tomography analysis unit 3 according to the first example embodiment includes, as functional blocks for realizing the functions thereof, a three-dimensional luminance data acquisition unit 301, an epidermis position extraction unit 302, a tomography image connection unit 303, a flattening transformation processing unit 304, and a fingerprint image extraction unit 305. Each of the three-dimensional luminance data acquisition unit 301, the epidermis position extraction unit 302, the tomography image connection unit 303, the flattening transformation processing unit 304, and the fingerprint image extraction unit 305 may be realized by the processor 101 (see FIG. 1), for example.

Three-dimensional luminance data acquisition unit 301 is configured to acquire the three-dimensional luminance data obtained by measuring the skin of a living body by using the optical coherence tomography unit 2. The three-dimensional luminance data acquisition unit 301 may newly acquire the three-dimensional luminance data by controlling the optical coherence tomography unit 2, or may acquire the three-dimensional luminance data by reading the three-dimensional luminance data acquired in advance from a storage medium such as the memory 102.

The epidermis position extraction unit 302 extracts an epidermis position for each tomography image of the three-dimensional luminance data acquired by the three-dimensional luminance data acquisition unit 301 (specifically, for each B-scan tomography image obtained by the scanning in the fast axis direction of the light beam). The epidermis position extraction unit 302 may extract coordinates indicating the epidermis position in the tomography image, for example.

The tomography image connection unit 303 is configured to adjust relative positions between the tomography images and to connect the tomography images, on the basis of the epidermis position extracted by the epidermis position extraction unit 302. More specifically, the tomography image connection unit 303 adjusts the relative positions to reduce a difference in the epidermis position between adjacent B-scan tomography images, on the basis of the extracted epidermis position. Then, the tomography image connection unit 303 connects the adjacent B-scan tomography images in which the position is adjusted, thereby to generate the three-dimensional luminance data (hereinafter referred to as "connected three-dimensional data" as appropriate).

The flattening transformation processing unit 304 is configured to perform transformation processing of flattening the epidermis in the connected three-dimensional data, on the basis of the epidermis position extracted by the epidermis position extraction unit 302. The flattening transformation processing unit 304 may flatten the epidermis by performing translation in the Z direction (i.e., the depth direction) of resetting the epidermis position to the origin, for example. In the following, the three-dimensional luminance data obtained by performing such transformation processing is referred to as "flattened three-dimensional data".

The fingerprint image extraction unit 305 is configured to extract a fingerprint image (i.e., a planar image indicating a pattern of the skin) corresponding to a predetermined extraction depth, from the flattened three-dimensional data obtained by the flattening transformation processing unit 304. The extraction depth here is a value set in advance in accordance with an extraction target, and may be a value corresponding to the epidermis, or a value corresponding to the dermis, for example. The fingerprint image extraction unit 305 may extract a plurality of fingerprints images from one piece of the flattened three-dimensional data, by changing the extraction depth. In addition to or instead of the fingerprint image, the fingerprint image extraction unit 305 may extract other data indicating the fingerprint (e.g., a feature quantity of the fingerprint), or the like.

(Flow of Operation)

Figure 4:
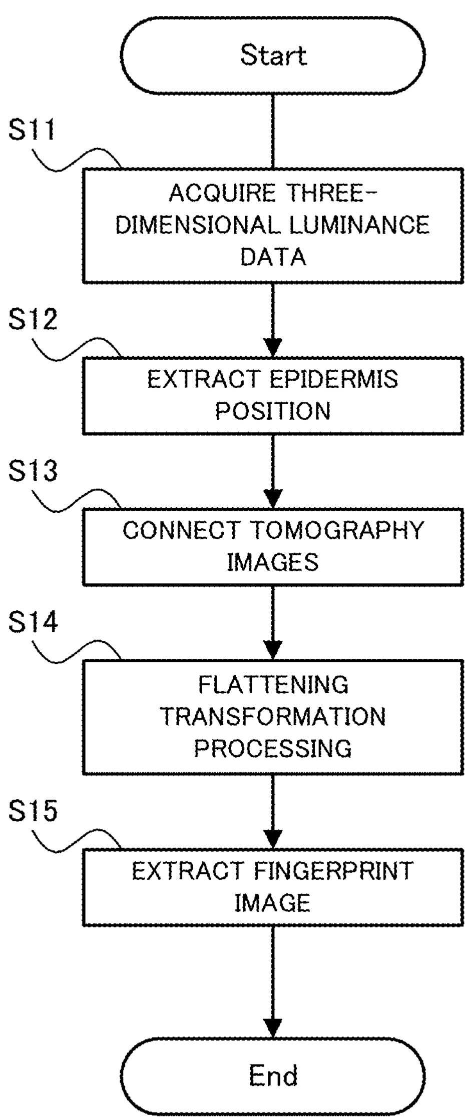
FIG. 4 is a flowchart illustrating a flow of a fingerprint extraction operation by the optical coherence tomography analysis unit according to the first example embodiment.

Next, with reference to FIG. 4, a flow of an operation of extracting the fingerprint image from the three-dimensional luminance data (hereinafter referred to as "fingerprint extraction operation" as appropriate) by the optical coherence tomography analysis unit 3 according to the first example embodiment, will be described. FIG. 4 is a flowchart illustrating the flow of the fingerprint extraction operation by the optical coherence tomography analysis unit according to the first example embodiment.

As illustrated in FIG. 4, in operation of the optical coherence tomography analysis unit 3 according to the first example embodiment, first, the three-dimensional luminance data acquisition unit 301 acquires the three-dimensional luminance data that are a measurement result of the optical coherence tomography unit 2 (step S11). The three-dimensional luminance data acquired by the three-dimensional luminance data acquisition unit 301 are outputted to the epidermis position extraction unit 302.

Subsequently, the epidermis position extraction unit 302 extracts the epidermis position for each tomography image, for the three-dimensional luminance data acquired by the three-dimensional luminance data acquisition unit 301 (step S12). Information about the epidermis position extracted by the epidermis position extraction unit 302 is outputted to each of the tomography image connection unit 303 and the flattening transformation processing unit 304.

Subsequently, the tomography image connection unit 303 adjusts the relative positions between the tomography images and connects the tomography images, on the basis of the epidermis position extracted by the epidermis position extraction unit 302, thereby to generate the connected three-dimensional data (step S13). The connected three-dimensional data generated by the tomography image connection unit 303 are outputted to the flattening transformation processing unit 304.

Subsequently, the flattening transformation processing unit 304 performs the transformation processing of flattening the epidermis in the connected three-dimensional data, on the basis of the epidermis position extracted by the epidermis position extraction unit 302, and generates the flattened three-dimensional data (step S14). The flattened three-dimensional data generated by the flattening transformation processing unit 304 are outputted to the fingerprint image extraction unit 305.

Subsequently, the fingerprint image extraction unit 305 extracts the fingerprint image corresponding to the predetermined extraction depth, from the flattened three-dimensional data obtained by the flattening transformation processing unit 304 (step S15). The fingerprint image extraction unit 305 may register (store) the extracted fingerprint image, as registration information. In this case, collation/verification processing using the registered fingerprint image (e.g., biometric authentication processing using a fingerprint) may be performed. A configuration in which the fingerprint image is used for the collation/verification processing will be described in detail in another example embodiment later.

Specific Operation Example

Figure 5:
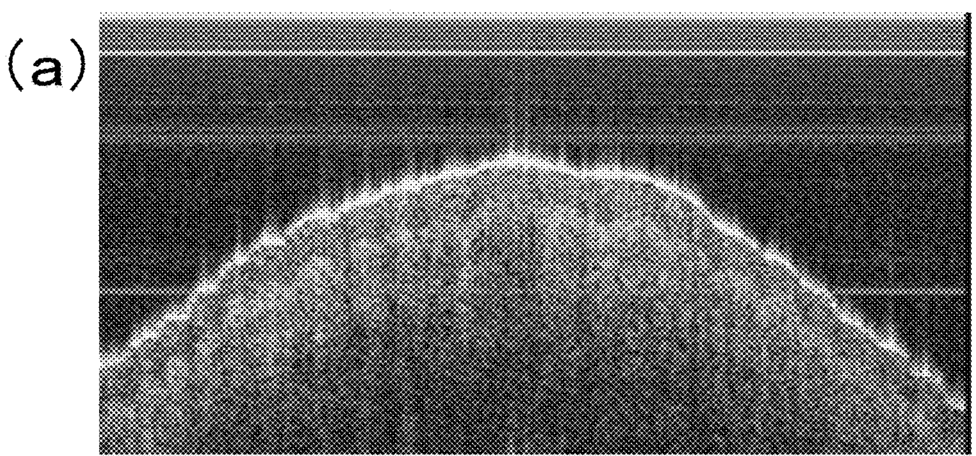
FIG. 5 is a plan view illustrating an example of three-dimensional luminance data acquired by the optical coherence tomography unit according to the first example embodiment.
Figure 5:
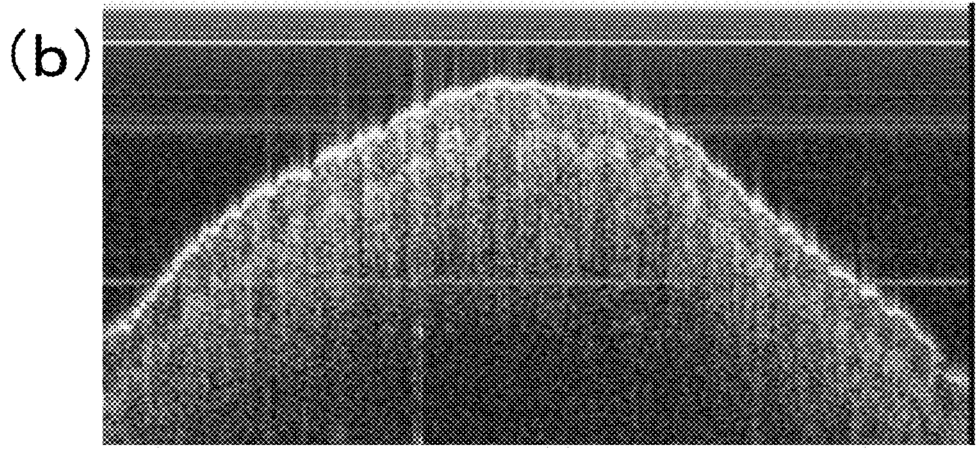
Figure 5:
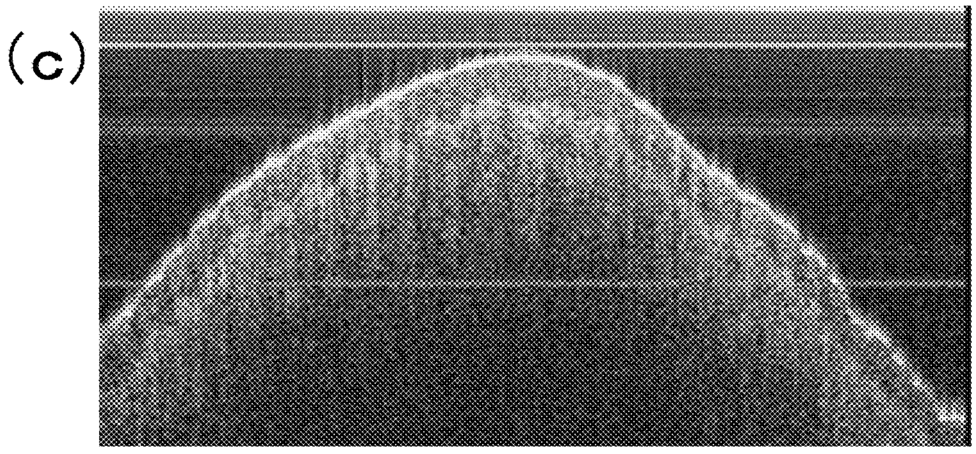
Figure 6:
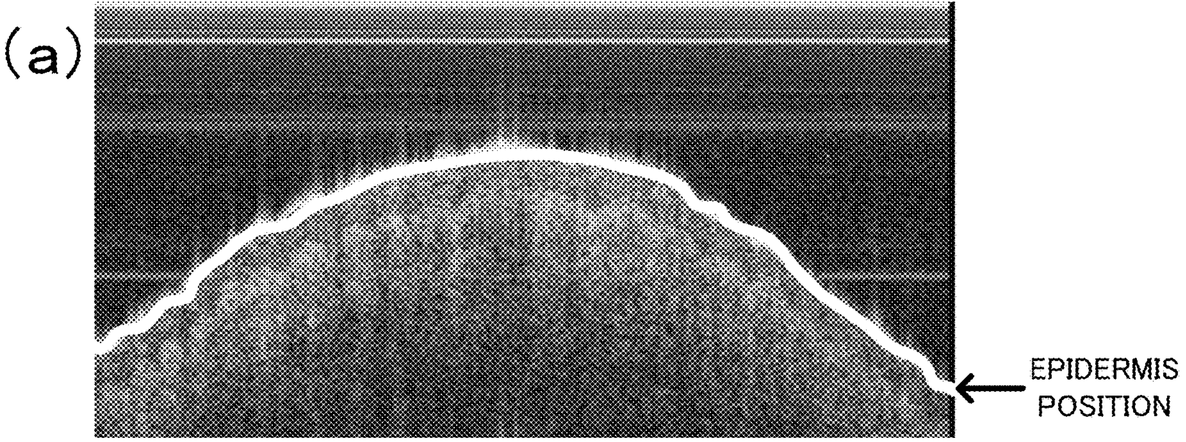
FIG. 6 is a plan view illustrating an extraction example of extracting an epidermis position by the optical coherence tomography analysis unit according to the first example embodiment.
Figure 6:
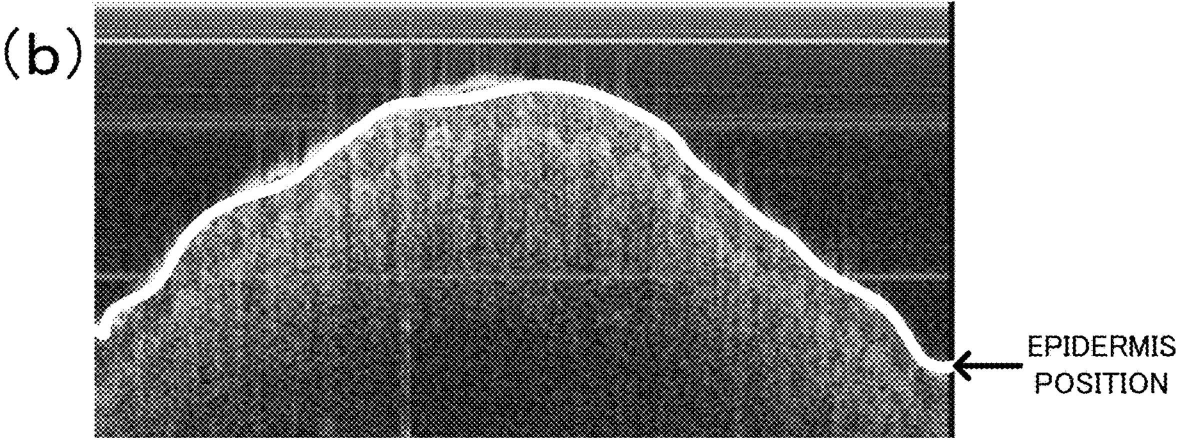
Figure 6:
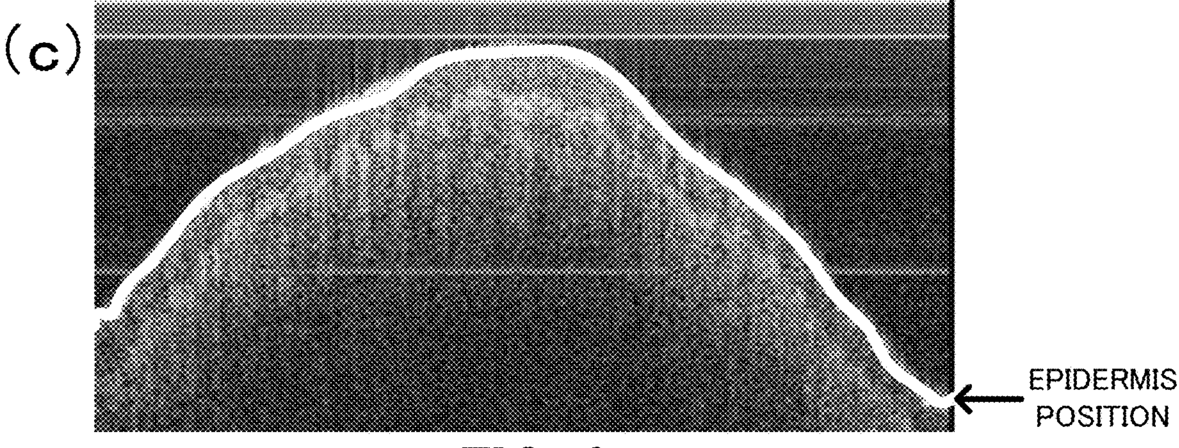
Figure 7:
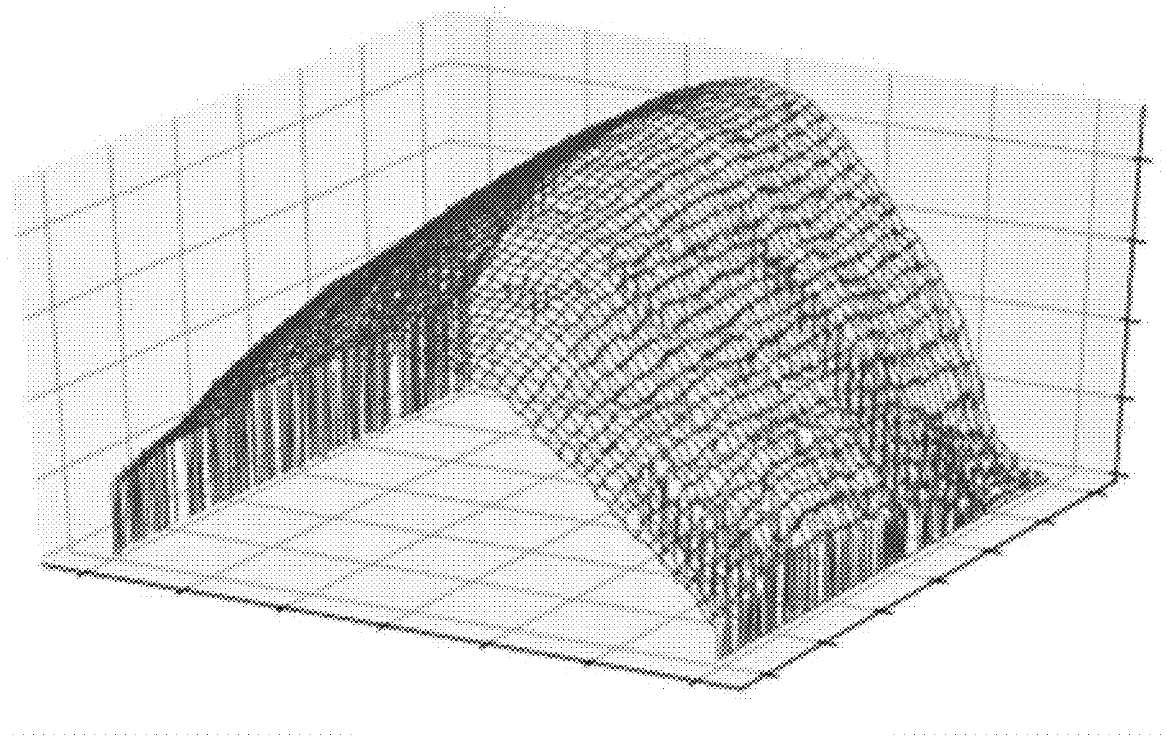
FIG. 7 is a three-dimensional diagram illustrating a connection example of connecting tomography images by the optical coherence tomography analysis unit according to the first example embodiment.
Figure 8:
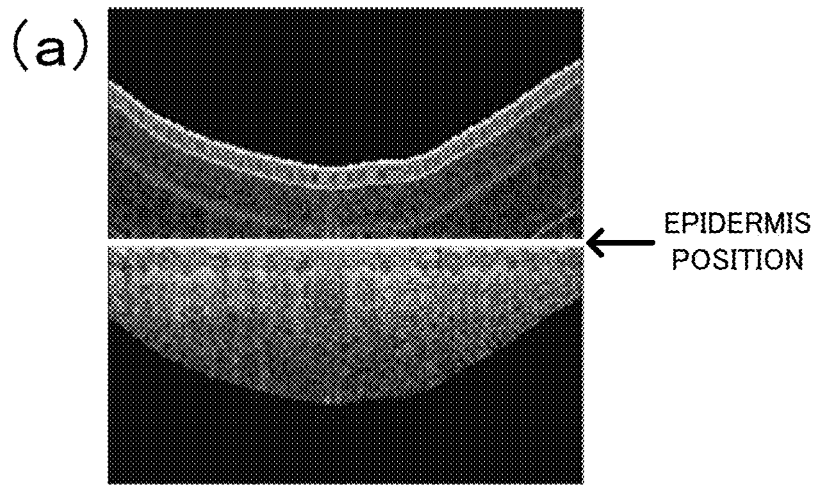
FIG. 8 is a plan view illustrating an example of flattening transformation processing by the optical coherence tomography analysis unit according to the first example embodiment.
Figure 8:
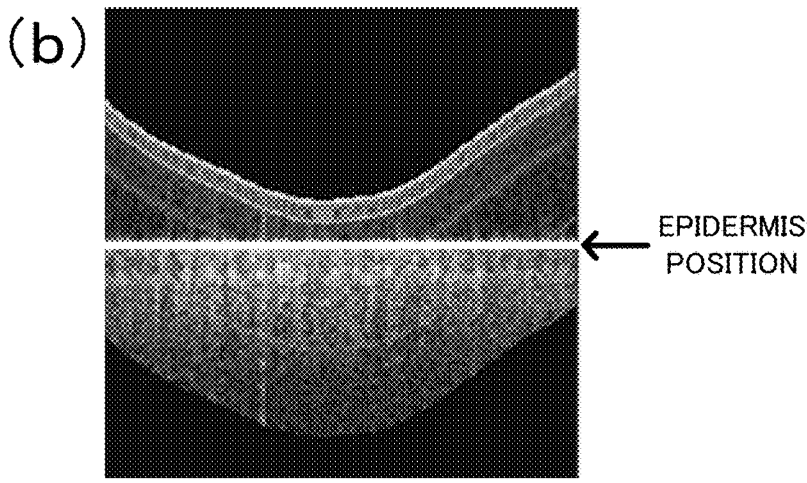
Figure 8:
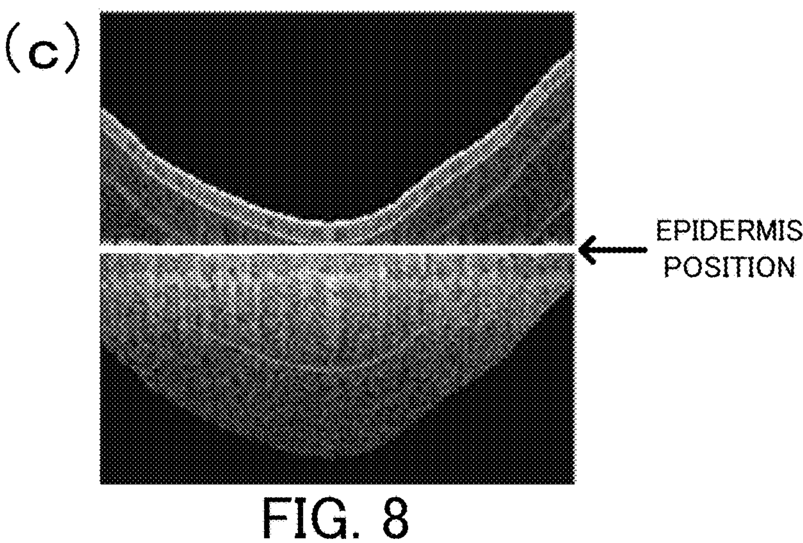
Figure 9:
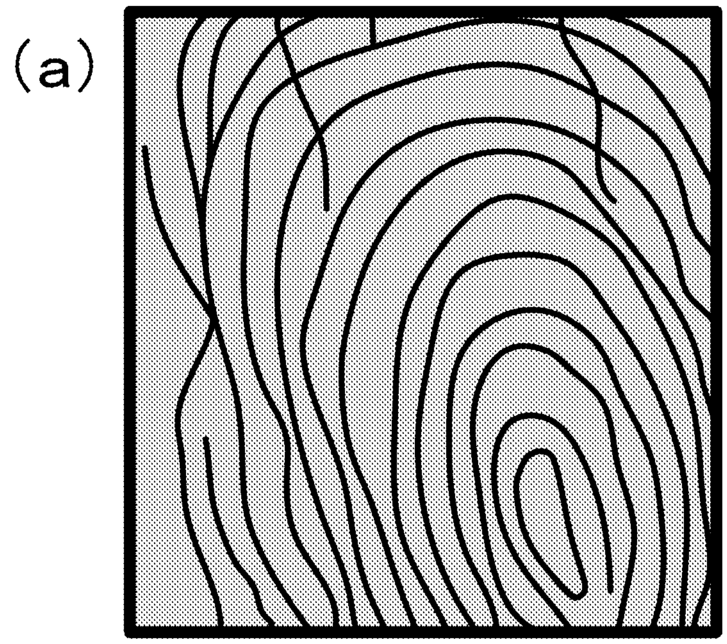
FIG. 9 is a plan view illustrating an extraction example of extracting a fingerprint image by the optical coherence tomography analysis unit according to the first example embodiment.
Figure 9:
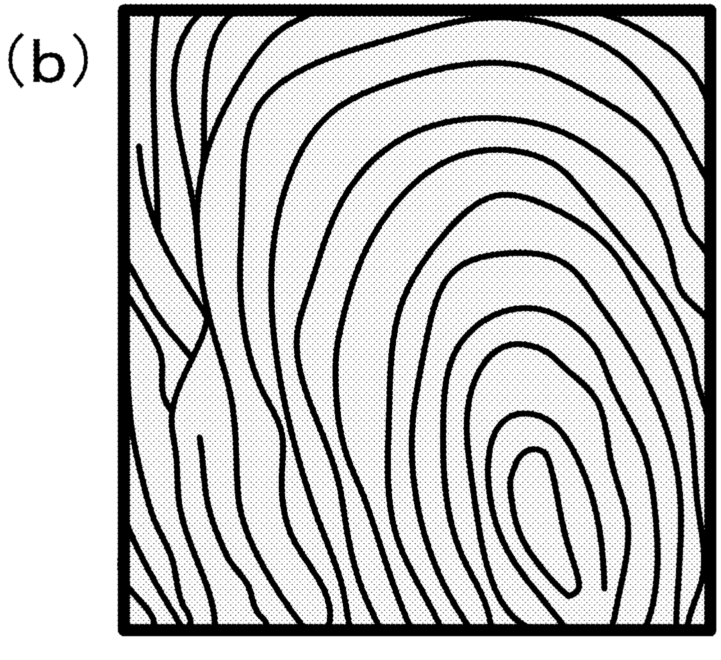

Next, with reference to FIG. 5 to FIG. 6, a specific operation example of the fingerprint extraction operation will be described. FIG. 5 is a plan view illustrating an example of the three-dimensional luminance data acquired by the optical coherence tomography unit according to the first example embodiment. FIG. 6 is a plan view illustrating an extraction example of extracting the epidermis position by the optical coherence tomography unit according to the first example embodiment. FIG. 7 is a three-dimensional diagram illustrating a connection example of connecting the tomography images by the optical coherence tomography analysis unit according to the first example embodiment. FIG. 8 is a plan view illustrating an example of the flattening transformation processing by the optical coherence tomography analysis unit according to the first example embodiment. FIG. 9 is a plan view illustrating an extraction example of extracting the fingerprint image by the optical coherence tomography analysis unit according to the first example embodiment.

The optical coherence tomography unit 2 images a finger of a living body in a noncontact manner, and generates three-dimensional luminance data where Nx=300, Ny=300, and Nz=256. This imaging is performed by setting the object light beam to be applied to 300 positions in the X direction that is the fast axis direction of the scanning, and to 300 positions in the Y direction that is the slow axis direction of the scanning, and by analyzing the interference light spectrum of the object light and the reference light to obtain the luminance data resolved/decomposed into 256 positions in the Z direction, in the light beam scanning unit 203 of the optical coherence tomography unit 2, and as a result, the three-dimensional luminance data about the finger of the living body are generated. The three-dimensional luminance data can be regarded as a set of Ny=300 B-scan tomography images at Nx×Nz=300×256. FIG. 5(*a*) to FIG. 5(*c*) illustrate three of the 300 B-scan tomography images, as an example of the acquired three-dimensional luminance data.

For the three-dimensional luminance data acquired by the three-dimensional luminance data acquisition unit 301 of the optical coherence tomography analysis unit 3, the epidermis position extraction unit 302 extracts the coordinates of the epidermis position for each B-scan tomography image. FIG. 6(*a*) to FIG. 6(*c*) illustrate results of extracting the epidermis position in three of the 300 B-scan tomography images. In a case where the finger is irradiated with the object light beam in a noncontact manner, usually, the object light is reflected at most at the epidermis position. Therefore, in the B-scan tomography image with a horizontal axis X and a vertical axis Z, a value Zs' of Z where the object light backscatter intensity (luminance) is maximized, is selected for each value of X. In many cases, however, the luminance is maximized at a non-epidermis position due to an influence of noise, and thus, outlier removal processing that takes into account that the epidermis is contiguous is performed.

Based on an extraction result of the epidermis position Zs extracted for each value of (X,Y) in the epidermis position extraction unit 302 of the optical coherence tomography analysis unit 3, the tomography image connection unit 303 adjusts the relative positions between the adjacent B-scan tomography images. When an epidermis position curve extracted on the B-scan tomography image is defined as Zs (X), the difference between the adjacent tomography images is adjusted to be minimized. The tomography image connection unit 303 generates the connected three-dimensional data, by connecting the tomography images in which the position is adjusted as described above (see FIG. 7).

On the connected three-dimensional data generated by the tomography image connecting portion 303 of the optical coherence tomography analysis unit 3, the flattening transformation processing unit 304 performs the transformation of flattening the epidermis position, on the basis of the extracted epidermis position. That is, it performs translation in the Z direction of resetting the epidermis position Zs extracted for each value of (X,Y), to the origin. Thus, the tomography image connection unit 303 obtains the flattened three-dimensional data. FIG. 8(*a*) to FIG. 8(*c*) illustrate results of epidermis flattening transformation processing performed on three of the 300 B-scan tomography images.

For the flattened three-dimensional data subjected to the epidermis flattening transformation processing, the fingerprint image extraction unit 305 extracts at least one of an epidermis fingerprint image and a dermis fingerprint image. In the flattened three-dimensional data on which the transformation processing is performed on the basis of the epidermis, Z=0 is a position of the epidermis. For this reason, the fingerprint image extraction unit 305 extracts the luminance data on an XY surface at Z=0, as the epidermis fingerprint image. The dermis fingerprint image may be extracted by selecting a position of Z on the basis of a feature quantity of an image sliced on the XY plane. At this time, an example of the feature quantity used, may be what extracts striped pattern sharpness, for a striped pattern such as a fingerprint. The striped pattern sharpness may be a feature quantity indicating that there are many stripes in the same shape formed by brightness and darkness in an image, such as for example, OCL (Orientation Certainty Level). The fingerprint image extraction unit 305 extracts the luminance data on the XY plane at the value of Z selected as a dermis position, as the dermis fingerprint image. The selection of the dermis position may be performed on each of small areas into which the XY surface is properly divided. The epidermis fingerprint image extracted by the above steps is illustrated in FIG. 9(*a*), and the dermis fingerprint image is illustrated in FIG. 9(*b*).

(Technical Effect)

Next, a technical effect obtained by the optical coherence tomography analysis apparatus 1 according to the first example embodiment will be described.

An imaging apparatus that images the skin of a living body, may not obtain a good image due to skin conditions in many cases. For example, a good image cannot be obtained in a case where the epidermis is dirty, is rough, or highly wrinkly. Especially in the case of using the OCT technique/technology, it takes time to generate the three-dimensional tomography data while scanning the light beam. Therefore, when it is attempted to measure the finger in a noncontact manner without fixing the finger, the position of the finger may move during light beam scanning, which is technically problematic. In addition, in the case of scanning the fingertip without touching a glass plate or the like, a dermis fingerprint is on a curved surface beneath the skin, and it is thus not easy to extract it as a planar fingerprint image with high accuracy.

According to the optical coherence tomography analysis apparatus 1 in the present example embodiment, however, extracts the epidermis position of the finger for each B-scan tomography image, and further adjusts the relative positions between the neighboring B-scan tomography images in view of the fact that the skin is contiguous, as described above. Here, since the B scan obtained by one scanning in the fast axis direction, takes a short time, an influence of movement of the finger is small. Therefore, according to the above-described operation, the three-dimensional luminance data in which the influence of movement of the finger is significantly suppressed, are obtained. Furthermore, by performing the flattening transformation processing on the basis of the extracted epidermis position, it is possible to extract the dermal fingerprint on the curved surface beneath the skin, or the like.

Second Example Embodiment

The optical coherence tomography analysis apparatus 1 according to a second example embodiment will be described with reference to FIG. 10 and FIG. 11. The second example embodiment is partially different from the first example embodiment only in the configuration and operation, and may be the same as the first example embodiment in the other parts. For this reason, a part that is different from the first example embodiment described above will be described in detail below, and a description of other overlapping parts will be omitted as appropriate.

(Apparatus Configuration)

First, with reference to FIG. 10, a configuration of the optical coherence tomography analysis apparatus 1 according to the second example embodiment will be described. FIG. 10 is a block diagram illustrating the configuration of the optical coherence tomography analysis apparatus according to the second example embodiment. In FIG. 10, the same components as those illustrated in FIG. 3 carry the same reference numerals.

Figure 10:
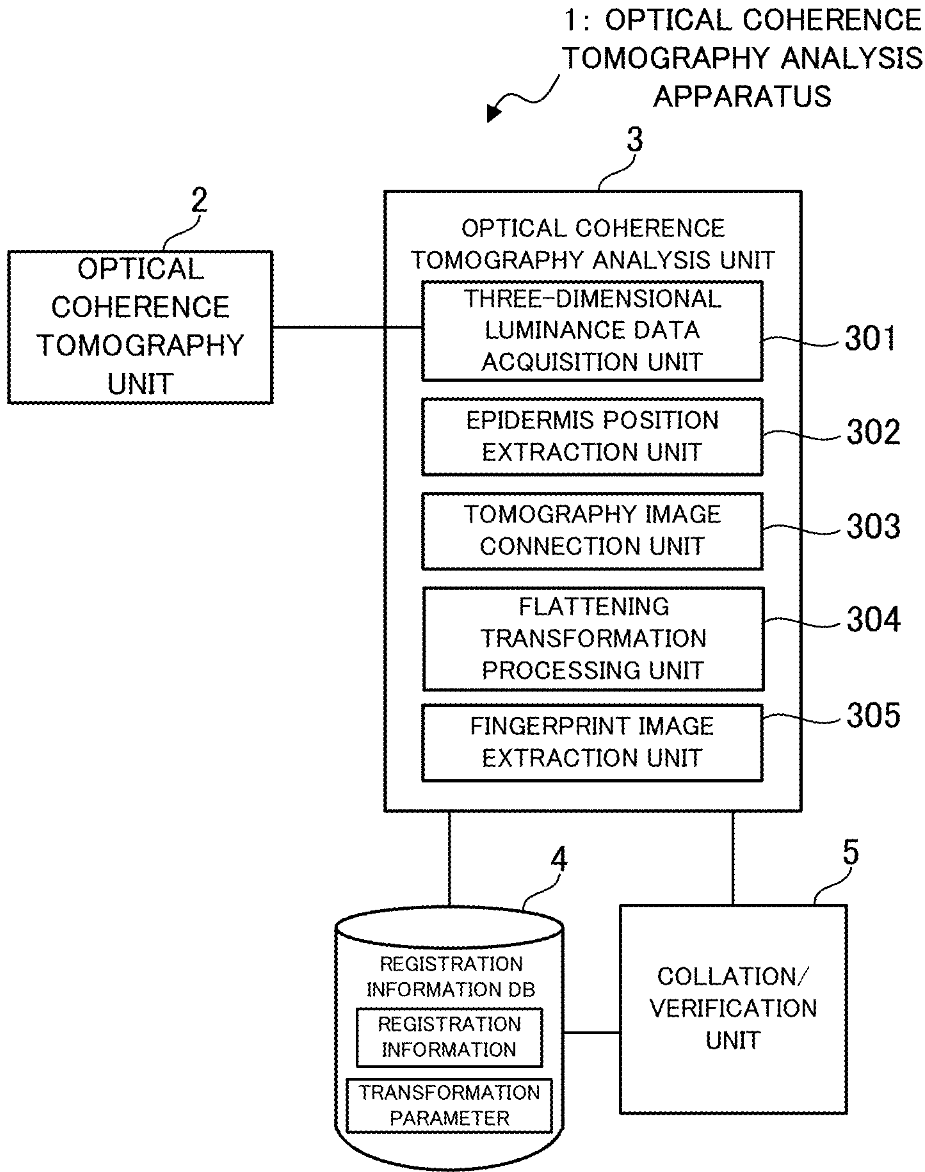
FIG. 10 is a block diagram illustrating a configuration of an optical coherence tomography analysis apparatus according to a second example embodiment.

As illustrated in FIG. 10, the optical coherence tomography analysis apparatus 1 according to the second example embodiment includes the optical coherence tomography unit 2, the optical coherence tomography analysis unit 3, a registration information database (DB) 4, and a collation/verification unit 5. That is, the optical coherence tomography analysis apparatus 1 according to the second example embodiment further includes the registration information database 4 and the collation/verification unit 5, in addition to the configuration in the first example embodiment (see FIG. 3).

The registration information database 4 is configured as a database including a storage apparatus, for example, and is configured to store the fingerprint image extracted by the fingerprint image extraction unit 305 (i.e., the extracted pattern of the skin), as registration information to be used in collation/verification. In addition, the registration information database 4 is configured to store a transformation parameter in association with the registration information. The transformation parameter is a parameter related to the transformation processing performed in the flattening transformation processing unit 304, and may indicate an amount of Z-direction translation when the epidermis position is reset to the origin, for example. More specifically, the transformation parameter may be a second average value obtained by averaging a first average value by a plurality of tomography images, wherein the first average value is an average value of the amounts of Z-direction translation in each of the tomography images, for example. Various types of information stored in the registration information database 4 is configured to be readable as appropriate by the collation/verification unit 5.

The collation/verification unit 5 is configured to perform collation/verification processing of collating/verifying a newly acquired fingerprint image (hereinafter referred to as a “collation image” as appropriate) with the registration information stored in the registration information database 4 (i.e., the fingerprint image registered in advance). This collation/verification processing may be performed as biometric authentication processing, for example. Furthermore, the collation/verification unit 5 according to the present example embodiment is especially configured to perform the collation/verification processing, on the basis of the transformation parameter stored in the registration information database 4. Specifically, the collation/verification unit 5 may compare the transformation parameter related to the collation image with the transformation parameter connected to the registration information, and may perform the collation/verification processing from the image with a smaller difference in the transformation parameter. That is, the collation/verification processing may be performed sequentially from the registration information whose transformation parameter is close to that of the collation image. In addition, the collation/verification unit 5 may compare the transformation parameter related to the collation image with the transformation parameter associated with the registration information, and may remove the image with a difference in the transformation parameter that is greater than a predetermined value, from a target of the collation/verification processing. That is, the registration information whose transformation parameter is far from that of the collation image, may not be used in the collation/verification processing.

The registration information database 4 and the collation/verification unit 5 may be integrally configured by hardware common to the optical coherence tomography analysis unit 3. That is, the registration information database 4 and the collation/verification unit 5 may be configured as functional blocks provided in the optical coherence tomography analysis unit 3.

(Collation/Verification Operation)

Next, with reference to FIG. 11, a flow of a collation/verification operation by the collation/verification unit 5 according to the second example embodiment will be described. FIG. 11 is a flowchart illustrating the flow of the a collation/verification operation by the optical coherence tomography analysis unit according to the second example embodiment.

Figure 11:
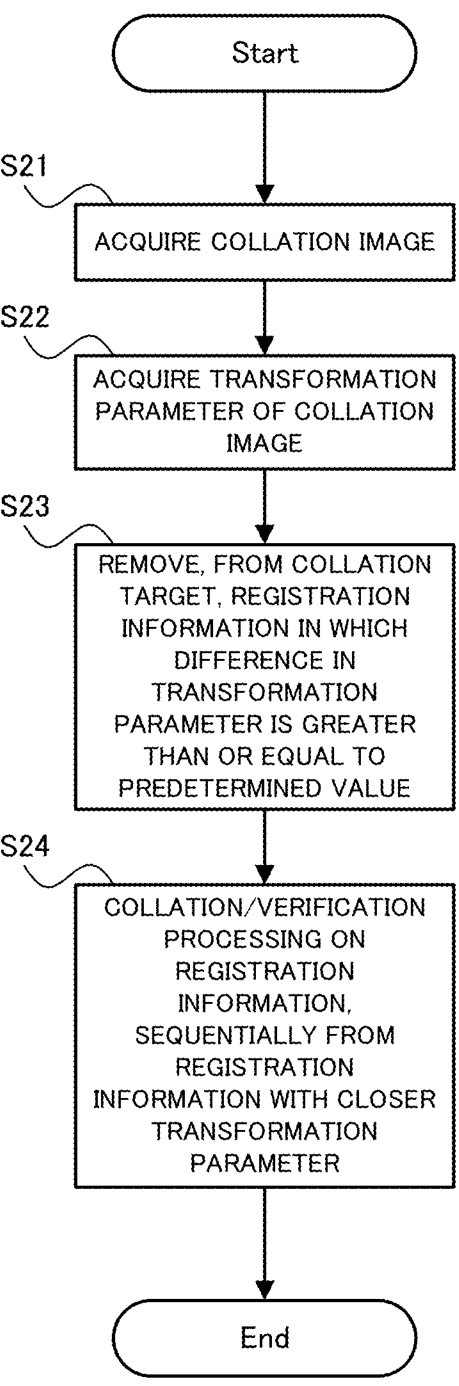
FIG. 11 is a flowchart illustrating a flow of a collation/verification operation by an optical coherence tomography analysis unit according to the second example embodiment.

As illustrated in FIG. 11, when the collation/verification operation by the collation/verification unit 5 according to the second example embodiment is started, first, the collation/verification unit 5 acquires the collation image (step S21). The collation image is typically acquired through the optical coherence tomography unit 2 and the optical coherence tomography analysis unit 3, but the collation/verification unit 5 may acquire the collation image in another path.

Next, the collation/verification unit 5 acquires the transformation parameter of the collation image (step S22). The collation/verification unit 5 removes, from a collation target, the registration information in which the difference in the transformation parameter is greater than or equal to a predetermined value, of the registration information registered in the registration information database 4 (step S23). The predetermined value may be a value set in advance, but may be a value that is changeable by the user, for example. Specifically, a user who would like to perform the collation/verification processing with more images, may increase the predetermined number and may reduce the number of pieces of registration information that are not the collation target. Alternatively, a user who would like to perform the collation/verification processing with fewer images, may reduce the predetermined number and may increase the number of pieces of registration information that are not the collation target.

Subsequently, the collation/verification unit 5 performs the collation/verification processing on the registration information that is the collation target (i.e., the registration information that is not removed from the collation target in the step S23), sequentially from the registration information with a smaller difference in the transformation parameter from that of the collation image (step S24). The collation/verification unit 5 may end the collation/verification processing when the collation/verification is successful.

(Technical Effect)

Next, a technical effect obtained by the optical coherence tomography analysis apparatus 1 according to the second example embodiment will be described.

As described in FIG. 10 and FIG. 11, in the optical coherence tomography analysis apparatus 1 according to the second example embodiment, the collation/verification processing is performed on the fingerprint image on the basis of the transformation parameter. In this way, it is possible to improve accuracy and speed of the collation/verification processing, as compared with a case of performing the collation/verification processing without consideration of the transformation parameter.

Third Example Embodiment

The optical coherence tomography analysis apparatus 1 according to a third example embodiment will be described with reference to FIG. 12. The third example embodiment is partially different from the first and second example embodiments only in the configuration and operation, and may be the same as the first and second example embodiments in the other parts. For this reason, a part that is different from each of the example embodiments described above will be described in detail below, and a description of other overlapping parts will be omitted as appropriate.

(Apparatus Configuration)

First, with reference to FIG. 12, a configuration of the optical coherence tomography analysis apparatus 1 according to the third example embodiment will be described. FIG. 12 is a block diagram illustrating the configuration of the optical coherence tomography analysis apparatus according to the third example embodiment. In FIG. 12, the same components as those illustrated in FIG. 10 carry the same reference numerals.

Figure 12:
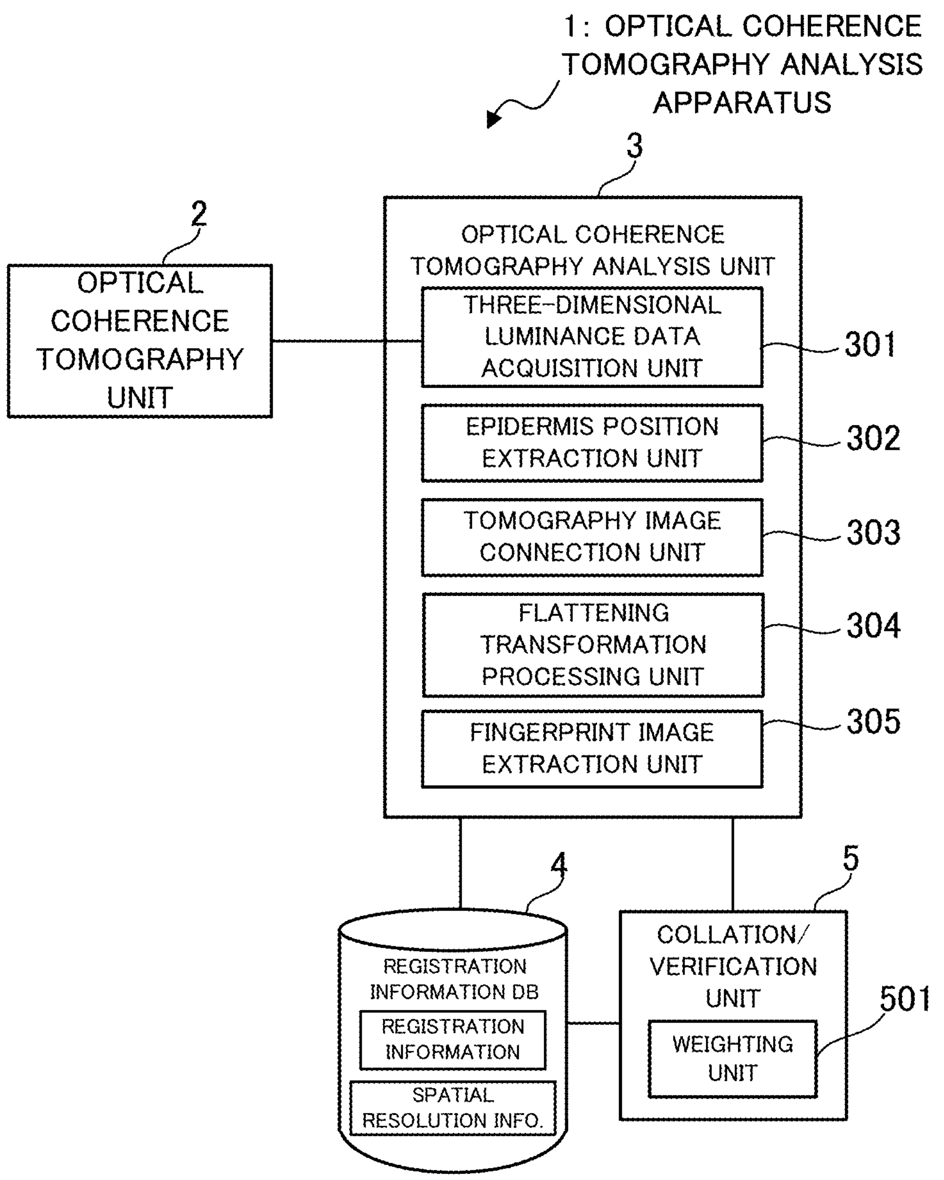
FIG. 12 is a block diagram illustrating a configuration of an optical coherence tomography analysis apparatus according to a third example embodiment.

As illustrated in FIG. 12, the optical coherence tomography analysis apparatus 1 according to the third example embodiment includes the optical coherence tomography unit 2, the optical coherence tomography analysis unit 3, the registration information database 4, and the collation/verification unit 5. That is, the optical coherence tomography analysis apparatus 1 according to the third example embodiment includes the same components as those in the second example embodiment (see FIG. 10).

The registration information database 4 according to the third example embodiment, however, is configured to store spatial resolution information indicating spatial resolution when the registration information is acquired, in addition to the registration information (i.e., the extracted fingerprint image). The spatial resolution is resolution when the three-dimensional luminance data are acquired in the optical coherence tomography unit 2. A diameter of the light beam applied to the skin of a living body varies depending o+-n the depth direction. For example, in a case where the light beam is applied to the finger in a noncontact state, a distance to the finger is changed by the irradiation position when the finger is bent, and thus, the diameter of the light beam applied varies depending on the distance. As a result, the spatial resolution is not constant, and there may be a high part and a low part. The registration information database 4 stores information indicating the spatial resolution, in association with the registration information.

Furthermore, the collation/verification unit 5 according to the third example embodiment includes a weighting unit 501. The weighting unit 501 is configured to perform weighting in accordance with the spatial resolution. For example, the weighting unit 501 may increase the weight in a high spatial resolution part, or may reduce the weight in a low spatial resolution part. The distance that allows high spatial resolution, depends on features of a lens attached to the optical coherence tomography unit 2. For this reason, the weighting unit 501 may hold the distance that allows the highest spatial resolution in advance, may determine a part close to the distance, to be a high spatial resolution part, and then may perform the weighting.

As a result of the weighting by the weighting unit 501, the collation/verification processing by the collation/verification unit 5 is performed in view of the weight (in other words, the spatial resolution) of each part. Specifically, a large weight part (i.e., a high spatial resolution part) has more influence on a collation/verification result, and a small weight part (i.e., a low spatial resolution part) has less influence on the collation/verification.

(Technical Effect)

Next, a technical effect obtained by the optical coherence tomography analysis apparatus 1 according to the third example embodiment will be described.

As described in FIG. 12, in the optical coherence tomography analysis apparatus 1 according to the third example embodiment, the collation/verification processing is performed after the weighting is performed in accordance with the spatial resolution. In this way, it is possible to improve the accuracy of the collation/verification processing, as compared with a case of performing the collation/verification processing without consideration of the spatial resolution.

Fourth Example Embodiment

The optical coherence tomography analysis apparatus 1 according to a fourth example embodiment will be described with reference to FIG. 13. The fourth example embodiment is partially different from the first to third example embodiments only in the configuration and operation, and may be the same as the first to third example embodiments in the other parts. For this reason, a part that is different from each of the example embodiments described above will be described in detail below, and a description of other overlapping parts will be omitted as appropriate.

(Apparatus Configuration)

First, with reference to FIG. 13, a configuration of the optical coherence tomography analysis apparatus 1 according to the fourth example embodiment will be described. FIG. 13 is a block diagram illustrating the configuration of the optical coherence tomography analysis apparatus according to the fourth example embodiment. In FIG. 13, the same components as those illustrated in FIG. 3 carry the same reference numerals.

Figure 13:
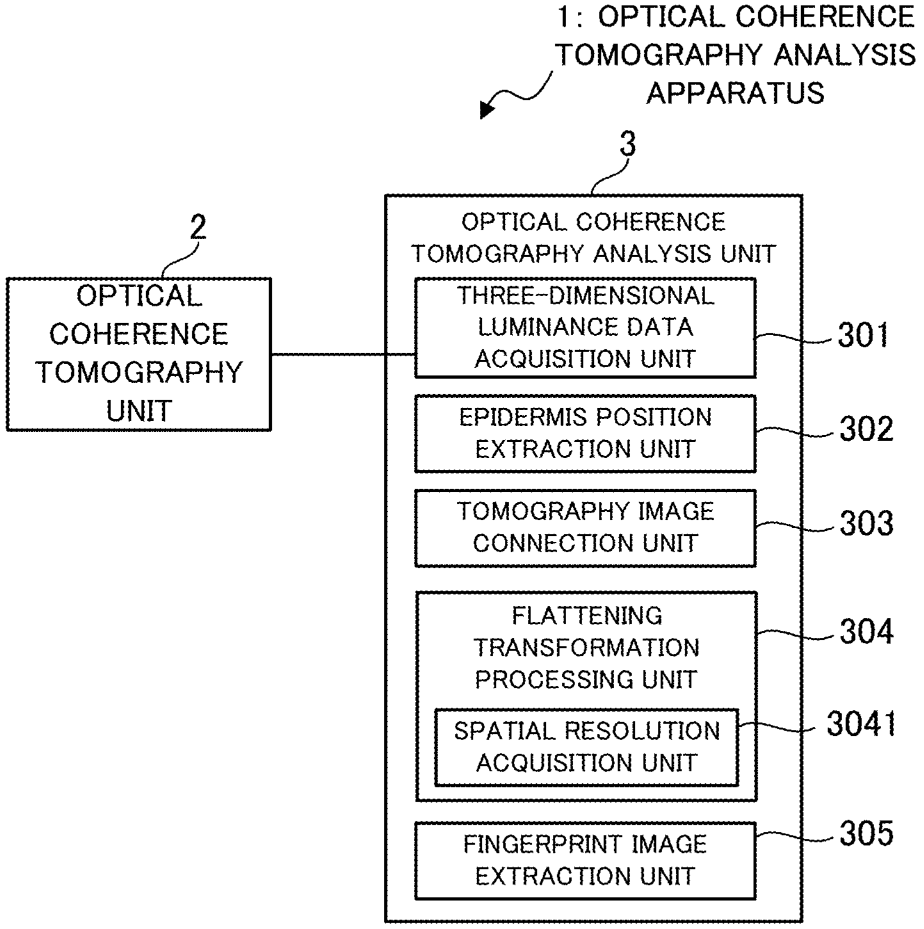
FIG. 13 is a block diagram illustrating a configuration of an optical coherence tomography analysis apparatus according to a fourth example embodiment.

As illustrated in FIG. 13, the optical coherence tomography analysis apparatus 1 according to the fourth example embodiment includes the optical coherence tomography unit 2 and the optical coherence tomography analysis unit 3. That is, the optical coherence tomography analysis apparatus 1 according to the fourth example embodiment includes the same components as those in the first example embodiment (see FIG. 3).

The flattening transformation processing unit 304 according to the fourth example embodiment, however, includes a spatial resolution acquisition unit 3041. The spatial resolution acquisition unit 3041 is configured to acquire spatial resolution information indicating spatial resolution when the three-dimensional luminance data are acquired in the optical coherence tomography unit 2. The spatial resolution information acquired by the spatial resolution acquisition unit 3041 is used for the transformation processing in the flattening transformation processing unit 304. Specifically, the flattening transformation processing unit 304 may perform the transformation processing on the basis of a high spatial resolution part. For example, the flattening transformation processing unit 304 may identify a position with the highest spatial resolution in an image, and may perform the transformation processing such that the position is set as a reference (i.e., by resetting the position to the origin). As described above, usually, the transformation processing is performed on the basis of the epidermis position, but in the flattening transformation processing unit 304 according to the present example embodiment, in a case where the spatial resolution of the epidermis position is low, the transformation processing may be performed on the basis of a part that is different from the epidermis position (e.g., the dermis position).

(Technical Effect)

Next, a technical effect obtained by the optical coherence tomography analysis apparatus 1 according to the fourth example embodiment will be described.

As described in FIG. 13, in the optical coherence tomography analysis apparatus 1 according to the fourth example embodiment, the transformation processing is performed on the basis of the high spatial resolution part. In this way, since the transformation processing can be performed by accurately identifying the reference part in the flattening, it is possible to improve the accuracy of the transformation processing.

Fifth Example Embodiment

The optical coherence tomography analysis apparatus 1 according to a fifth example embodiment will be described with reference to FIG. 14. The fifth example embodiment is partially different from the first to fourth example embodiments only in the configuration and operation, and may be the same as the first and fourth example embodiments in the other parts. For this reason, a part that is different from each of the example embodiments described above will be described in detail below, and a description of other overlapping parts will be omitted as appropriate.

(Apparatus Configuration)

First, with reference to FIG. 14, a configuration of the optical coherence tomography analysis apparatus 1 according to the fifth example embodiment will be described. FIG. 14 is a block diagram illustrating the configuration of the optical coherence tomography analysis apparatus according to the fifth example embodiment. In FIG. 14, the same components as those illustrated in FIG. 10 carry the same reference numerals.

Figure 14:
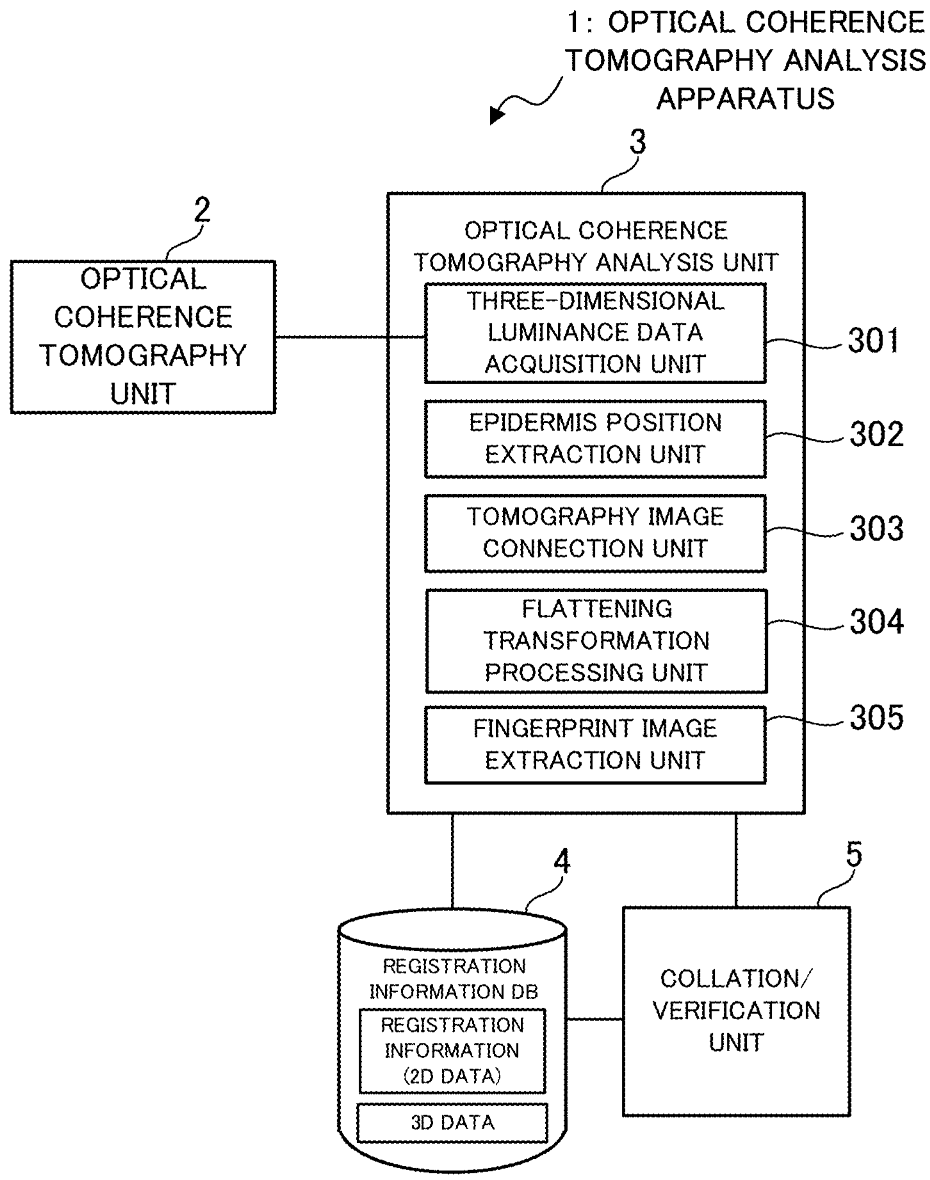
FIG. 14 is a block diagram illustrating a configuration of an optical coherence tomography analysis apparatus according to a fifth example embodiment.

As illustrated in FIG. 14, the optical coherence tomography analysis apparatus 1 according to the fifth example embodiment includes the optical coherence tomography unit 2, the optical coherence tomography analysis unit 3, the registration information database 4, and the collation/verification unit 5. That is, the optical coherence tomography analysis apparatus 1 according to the fifth example embodiment includes the same components as those in the second example embodiment (see FIG. 10) and the third example embodiment (see FIG. 12).

The registration information database 4 according to the fifth example embodiment, however, is configured to store three-dimensional data, in addition to the registration information (i.e., the extracted fingerprint image: two-dimensional data). The three-dimensional data here are three-dimensional data about the skin of a living body illustrated by the three-dimensional luminance data (e.g., data including a three-dimensional shape of a finger). The three-dimensional data are stored in association with the registration information. The three-dimensional data may be data generated by connecting a plurality of tomography images by the tomography image connection unit 303.

The registration information stored in the registration information database 4 and the three-dimensional data may be used for the collation/verification processing in the collation/verification unit 5. For example, the collation/verification unit 5 may select one of the registration information and the three-dimensional data, and may perform the collation/verification processing. Specifically, in a case where the two-dimensional data are acquired as the collation image, the collation/verification unit 5 may use the registration information that is the two-dimensional data for the collation/verification, and in a case where the three-dimensional data are acquired as the collation image, the collation/verification unit 5 may use the three-dimensional data for the collation/verification.

Alternatively, the collation/verification unit 5 may perform the collation/verification processing, by using both the registration information and the three-dimensional data. Specifically, the collation/verification unit 5 may determine that the collation/verification is successful in a case where both the registration information and the three-dimensional data match the collation image, and may determine that the collation/verification is failed when one of them does not match the collation image.

Alternatively, the collation/verification unit 5 may perform the collation/verification processing after narrowing down the registration information serving as the collation target by using the three-dimensional data. For example, the collation/verification unit 5 calculates a distribution of depth and curvature of the finger from the three-dimensional data stored in the registration information database 4, and compares them with those obtained from the three-dimensional data for collation/verification. In a case where there is a large difference in the distribution of depth and curvature of the finger, the collation/verification unit 5 may remove the registration information associated with the three-dimensional data, from the collation target. In other words, the collation/verification processing may be performed by targeting only the registration information associated with the three-dimensional data in which the distribution of depth and curvature of the finger is close to those obtained from the three-dimensional data for collation/verification.

(Technical Effect)

Next, a technical effect obtained by the optical coherence tomography analysis apparatus 1 according to the fifth example embodiment will be described.

As described in FIG. 14, in the optical coherence tomography analysis apparatus 1 according to the fifth example embodiment, the registration information database stores the two-dimensional data and the three-dimensional data. In this way, it is possible to improve the accuracy and speed of the collation/verification processing, as compared with a case of performing the collation/verification processing by using only the two-dimensional data.

A processing method in which a program for allowing the configuration in each of the example embodiments to operate so as to realize the functions of each example embodiment is recorded on a recording medium, and in which the program recorded on the recording medium is read as a code and executed on a computer, is also included in the scope of each of the example embodiments. That is, a computer-readable recording medium is also included in the range of each of the example embodiments. Not only the recording medium on which the above-described program is recorded, but also the program itself is also included in each example embodiment.

The recording medium to use may be, for example, a floppy disk (registered trademark), a hard disk, an optical disk, a magneto-optical disk, a CD-ROM, a magnetic tape, a nonvolatile memory card, or a ROM. Furthermore, not only the program that is recorded on the recording medium and executes processing alone, but also the program that operates on an OS and executes processing in cooperation with the functions of expansion boards and another software, is also included in the scope of each of the example embodiments. Furthermore, the program itself may be stored in a server, and a part or all of the program may be downloaded from the server to a user terminal.

<Supplementary Notes>

The example embodiments described above may be further described as, but not limited to, the following Supplementary Notes below.

(Supplementary Note 1)

An optical coherence tomography analysis apparatus according to Supplementary Note 1 is an optical coherence tomography analysis apparatus including: an acquisition unit that performs optical coherence tomography by applying a light beam to a skin while performing two-dimensional scanning, and that acquires three-dimensional luminance data about the skin; a position extraction unit that extracts an epidermis position of the skin, for each tomography image obtained by scanning in a fast axis direction of the light beam, in the three-dimensional luminance data about the skin; a connection unit that generates connected three-dimensional data, by adjusting relative positions between tomography images and connecting the tomography images, on the basis of an extraction result of the epidermis position of the skin; a flattening unit that generates flattened three-dimensional data, by performing transformation processing of flattening epidermis on the connected three-dimensional data, on the basis of an extraction result of the epidermis position of the skin; and a pattern extraction unit that extracts a pattern of the skin corresponding to a predetermined extraction depth, from the flattened three-dimensional data.

(Supplementary Note 2)

An optical coherence tomography analysis apparatus according to Supplementary Note 2 is the optical coherence tomography analysis apparatus according to Supplementary Note 1, further including: a storage unit that stores the pattern of the skin extracted by the pattern extraction unit, as registration information; and a collation/verification unit that performs collation/verification processing of collating/verifying a pattern of the skin newly acquired with the registration information stored in the storage unit, wherein the storage unit stores the registration information and a transformation parameter related to the transformation processing performed by the flattening unit, in association with each other, and the collation/verification unit performs the collation/verification processing on the basis of the transformation parameter.

(Supplementary Note 3)

An optical coherence tomography analysis apparatus according to Supplementary Note 3 is the Optical coherence tomography analysis apparatus according to Supplementary Note 1 or 2, further including: a storage unit that stores the pattern of the skin extracted by the pattern extraction unit, as registration information; and a collation/verification unit that performs collation/verification processing of collating/verifying a pattern of the skin newly acquired with the registration information stored in the storage unit, wherein the collation/verification unit performs the collation/verification processing, by performing weighting corresponding to spatial resolution when the optical coherence tomography is performed.

(Supplementary Note 4)

An optical coherence tomography analysis apparatus according to Supplementary Note 4 is the optical coherence tomography analysis apparatus according to any one of Supplementary Notes 1 to 3, wherein the flattening unit performs the transformation processing, on the basis of a high spatial resolution part when the optical coherence tomography is performed.

(Supplementary Note 5)

An optical coherence tomography analysis apparatus according to Supplementary Note 5 is the optical coherence tomography analysis apparatus according to any one of Supplementary Notes 1 to 4, further including: a storage unit that stores the pattern of the skin extracted by the pattern extraction unit, as registration information; and a collation/verification unit that performs collation/verification processing of collating/verifying a pattern of the skin newly acquired with the registration information stored in the storage unit, wherein the storage unit stores the registration information and the connected three-dimensional data in association with each other, and the collation/verification unit performs the collation/verification processing, by using the connected three-dimensional data, in addition to the registration information.

(Supplementary Note 6)

An optical coherence tomography analysis method according to Supplementary Note 6 is an optical coherence tomography analysis method that is executed by at least one computer, the optical coherence tomography analysis method including: performing optical coherence tomography by applying a light beam to a skin while performing two-dimensional scanning, and acquiring three-dimensional luminance data about the skin; extracting an epidermis position of the skin, for each tomography image obtained by scanning in a fast axis direction of the light beam, in the three-dimensional luminance data about the skin; generating connected three-dimensional data, by adjusting relative positions between tomography images and connecting the tomography images, on the basis of an extraction result of the epidermis position of the skin; generating flattened three-dimensional data, by performing transformation processing of flattening epidermis on the connected three-dimensional data, on the basis of an extraction result of the epidermis position of the skin; and extracting a pattern of the skin corresponding to a predetermined extraction depth, from the flattened three-dimensional data.

(Supplementary Note 7)

A recording medium according to Supplementary Note 7 is a recording medium on which a computer program that allows at least one computer to execute an optical coherence tomography analysis method is recorded, the optical coherence tomography analysis method including: performing optical coherence tomography by applying a light beam to a skin while performing two-dimensional scanning, and acquiring three-dimensional luminance data about the skin; extracting an epidermis position of the skin, for each tomography image obtained by scanning in a fast axis direction of the light beam, in the three-dimensional luminance data about the skin; generating connected three-dimensional data, by adjusting relative positions between tomography images and connecting the tomography images, on the basis of an extraction result of the epidermis position of the skin; generating flattened three-dimensional data, by performing transformation processing of flattening epidermis on the connected three-dimensional data, on the basis of an extraction result of the epidermis position of the skin; and extracting a pattern of the skin corresponding to a predetermined extraction depth, from the flattened three-dimensional data.

(Supplementary Note 8)

A computer program according to Supplementary Note 8 is a computer program that allows at least one computer to execute an optical coherence tomography analysis method, the optical coherence tomography analysis method including: performing optical coherence tomography by applying a light beam to a skin while performing two-dimensional scanning, and acquiring three-dimensional luminance data about the skin; extracting an epidermis position of the skin, for each tomography image obtained by scanning in a fast axis direction of the light beam, in the three-dimensional luminance data about the skin; generating connected three-dimensional data, by adjusting relative positions between tomography images and connecting the tomography images, on the basis of an extraction result of the epidermis position of the skin; generating flattened three-dimensional data, by performing transformation processing of flattening epidermis on the connected three-dimensional data, on the basis of an extraction result of the epidermis position of the skin; and extracting a pattern of the skin corresponding to a predetermined extraction depth, from the flattened three-dimensional data.

(Supplementary Note 9)

An optical coherence tomography analysis system according to Supplementary Note 9 is an optical coherence tomography analysis system including: an acquisition unit that performs optical coherence tomography by applying a light beam to a skin while performing two-dimensional scanning, and that acquires three-dimensional luminance data about the skin; a position extraction unit that extracts an epidermis position of the skin, for each tomography image obtained by scanning in a fast axis direction of the light beam, in the three-dimensional luminance data about the skin; a connection unit that generates connected three-dimensional data, by adjusting relative positions between tomography images and connecting the tomography images, on the basis of an extraction result of the epidermis position of the skin; a flattening unit that generates flattened three-dimensional data, by performing transformation processing of flattening epidermis on the connected three-dimensional data, on the basis of an extraction result of the epidermis position of the skin; and a pattern extraction unit that extracts a pattern of the skin corresponding to a predetermined extraction depth, from the flattened three-dimensional data.

This disclosure is not limited to the examples described above and is allowed to be changed, if desired, without departing from the essence or spirit of this disclosure which can be read from the claims and the entire specification. An optical coherence tomography analysis apparatus, an optical coherence tomography analysis method, and a recording medium with such changes are also intended to be within the technical scope of this disclosure.

DESCRIPTION OF REFERENCE CODES

1 Optical coherence tomography analysis apparatus
2 Optical coherence tomography unit
3 Optical coherence tomography analysis unit
4 Registration information database
5 Collation/verification unit
101 Processor
102 Memory
103 Communication interface
104 Input apparatus
105 Output apparatus
201 Wavelength-swept laser source
202 Light interference/light receiving unit
203 Light beam scanning unit
204 Signal processing/control unit
205 Measurement target
211 Circulator
212 Brancher/coupler
213 Reference light mirror
214 Balanced optical receiver
215 Fiber collimator
216 Irradiation optical system
301 Three-dimensional luminance data acquisition unit
302 Epidermis position extraction unit
303 Tomography image connection unit
304 Flattening transformation processing unit
305 Fingerprint image extraction unit
501 Weighting unit
3041 Spatial resolution acquisition unit

What is claimed is:

1. An optical coherence tomography analysis apparatus comprising:

at least one memory that is configured to store instructions; and at least one processor that is configured to execute the instructions to:

perform optical coherence tomography by applying a light beam to a skin while performing two-dimensional scanning, and acquires three-dimensional luminance data about the skin;

extract an epidermis position of the skin, for each tomography image obtained by scanning in a fast axis direction of the light beam, in the three-dimensional luminance data about the skin;

generate connected three-dimensional data, by adjusting relative positions between tomography images and connecting the tomography images, on the basis of an extraction result of the epidermis position of the skin;

generate flattened three-dimensional data, by performing transformation processing of flattening epidermis on the connected three-dimensional data, on the basis of an extraction result of the epidermis position of the skin; and extract a pattern of the skin corresponding to a predetermined extraction depth, from the flattened three-dimensional data.

2. The optical coherence tomography analysis apparatus according to claim 1, wherein the at least one processor is configured to execute the instructions to:

store the pattern of the skin extracted, as registration information;

perform collation/verification processing of collating/verifying a pattern of the skin newly acquired with the registration information stored;

store the registration information and a transformation parameter related to the transformation processing performed, in association with each other; and perform the collation/verification processing on the basis of the transformation parameter.

3. The Optical coherence tomography analysis apparatus according to claim 1, wherein the at least one processor is configured to execute the instructions to:

store the pattern of the skin extracted, as registration information;

perform collation/verification processing of collating/verifying a pattern of the skin newly acquired with the registration information stored; and perform the collation/verification processing, by performing weighting corresponding to spatial resolution when the optical coherence tomography is performed.

4. The optical coherence tomography analysis apparatus according to claim 1, wherein the at least one processor is configured to execute the instructions to perform the transformation processing, on the basis of a high spatial resolution part when the optical coherence tomography is performed.

5. The optical coherence tomography analysis apparatus according to claim 1, wherein the at least one processor is configured to execute the instructions to:

store the pattern of the skin extracted, as registration information;

perform collation/verification processing of collating/verifying a pattern of the skin newly acquired with the registration information stored;

store the registration information and the connected three-dimensional data in association with each other; and perform the collation/verification processing, by using the connected three-dimensional data, in addition to the registration information.

6. An optical coherence tomography analysis method that is executed by at least one computer, the optical coherence tomography analysis method comprising:

performing optical coherence tomography by applying a light beam to a skin while performing two-dimensional scanning, and acquiring three-dimensional luminance data about the skin;

extracting an epidermis position of the skin, for each tomography image obtained by scanning in a fast axis direction of the light beam, in the three-dimensional luminance data about the skin;

generating connected three-dimensional data, by adjusting relative positions between tomography images and connecting the tomography images, on the basis of an extraction result of the epidermis position of the skin;

generating flattened three-dimensional data, by performing transformation processing of flattening epidermis on the connected three-dimensional data, on the basis of an extraction result of the epidermis position of the skin; and extracting a pattern of the skin corresponding to a predetermined extraction depth, from the flattened three-dimensional data.

7. A non-transitory recording medium on which a computer program that allows at least one computer to execute an optical coherence tomography analysis method is recorded, the optical coherence tomography analysis method including:

performing optical coherence tomography by applying a light beam to a skin while performing two-dimensional scanning, and acquiring three-dimensional luminance data about the skin;

extracting an epidermis position of the skin, for each tomography image obtained by scanning in a fast axis direction of the light beam, in the three-dimensional luminance data about the skin;

generating connected three-dimensional data, by adjusting relative positions between tomography images and connecting the tomography images, on the basis of an extraction result of the epidermis position of the skin;

generating flattened three-dimensional data, by performing transformation processing of flattening epidermis on the connected three-dimensional data, on the basis of an extraction result of the epidermis position of the skin; and extracting a pattern of the skin corresponding to a predetermined extraction depth, from the flattened three-dimensional data.

* * * * *